United States Patent [19]

Isogai et al.

[11] Patent Number: 5,341,180
[45] Date of Patent: Aug. 23, 1994

[54] OPHTHALMIC PHOTOGRAPHING APPARATUS

[75] Inventors: Naoki Isogai; Kenya Ozaki, both of Aichi, Japan

[73] Assignee: Nidek Co., Ltd., Aichi, Japan

[21] Appl. No.: 901,984

[22] Filed: Jun. 22, 1992

[30] Foreign Application Priority Data

Jun. 29, 1991 [JP] Japan ................................. 3-185448

[51] Int. Cl.$^5$ .............................................. A61B 3/14
[52] U.S. Cl. ..................................... 351/206; 351/211; 351/214; 351/221
[58] Field of Search ............... 351/205, 206, 211, 214, 351/221; 345/207

[56] References Cited

U.S. PATENT DOCUMENTS

| | | | |
|---|---|---|---|
| 4,196,980 | 4/1990 | Heine | 351/211 |
| 4,423,936 | 1/1984 | Johnson | 354/403 |
| 4,786,162 | 11/1988 | Fujiwara et al. | 351/206 |
| 4,901,101 | 2/1990 | Ishida et al. | 354/403 |
| 5,071,245 | 12/1991 | Fukuma et al. | 351/211 |
| 5,291,231 | 3/1994 | Hideshima et al. | 351/206 |

Primary Examiner—Loha Ben
Assistant Examiner—Thomas Robbins
Attorney, Agent, or Firm—Finnegan, Henderson, Farabow, Garrett & Dunner

[57] ABSTRACT

Ophthalmic photographing an image of an eye to be examined comprises: frame memory for memorizing the image data of the photographed eye, light detecting device for detecting an amount of the light emitted from a light source for photographing, correcting device for correcting a density of the image data memorized in the frame memory by comparing the amount of the light detected by the light detecting device with predetermined amount of reference light. Therefore the ophthalmic photographing apparatus can display the image having a constant density, even though the amount of the light emitted from the light source for photographing changes.

14 Claims, 3 Drawing Sheets

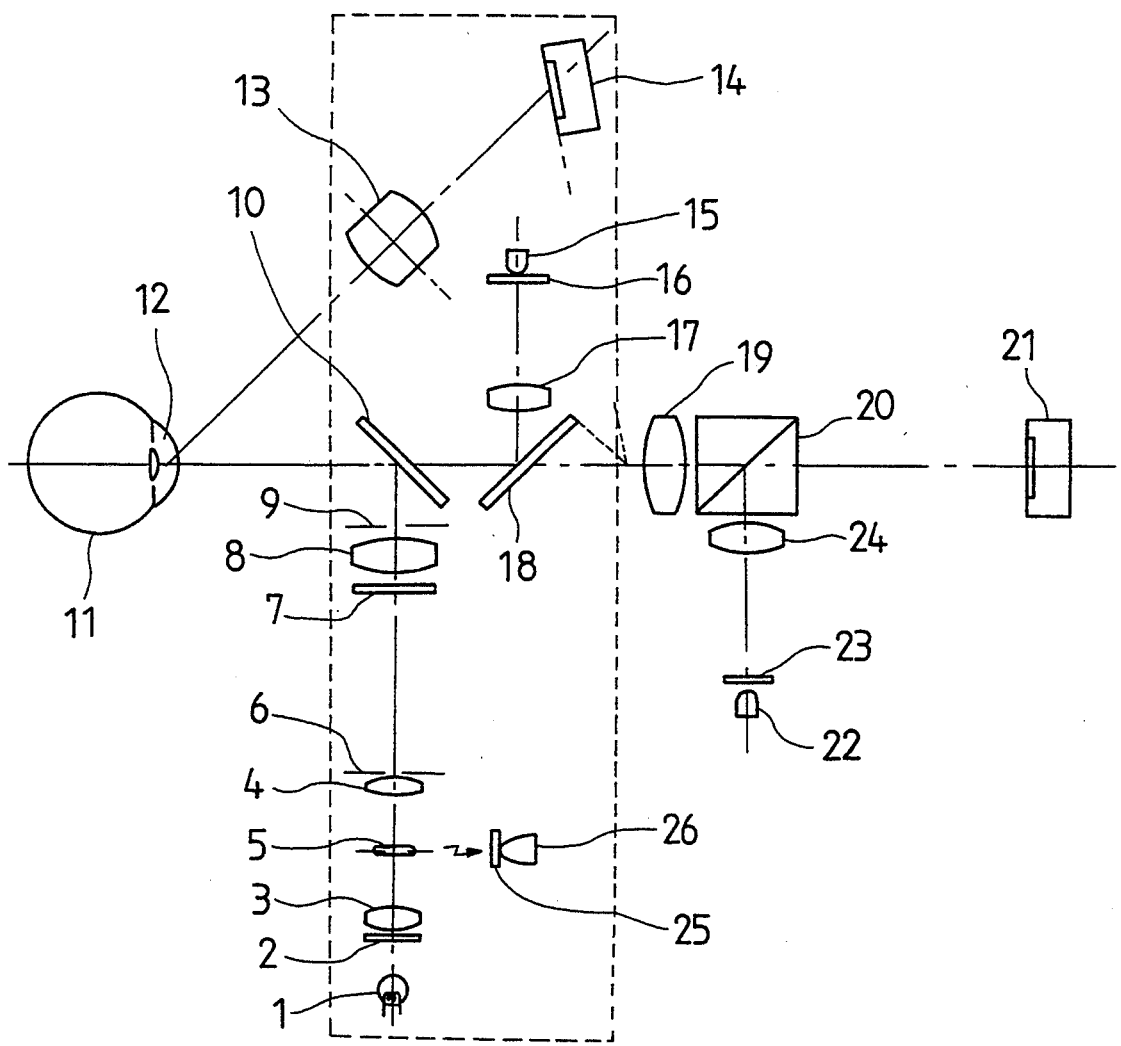
F I G . 1

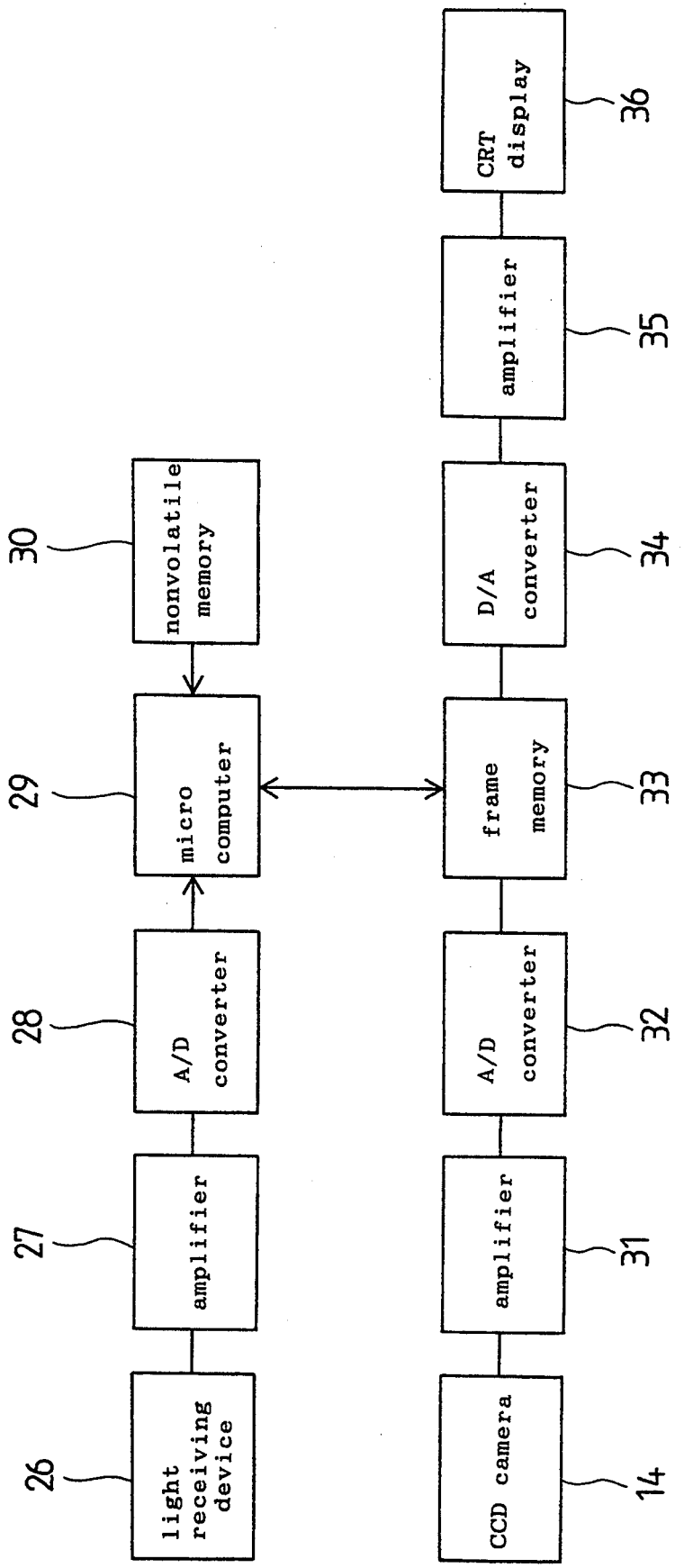

OPHTHALMIC PHOTOGRAPHING APPARATUS

BACKGROUND OF THE INVENTION

1. Field of the Invention

The present invention relates to an ophthalmic apparatus for photographing various images of the eye to be diagnosed.

2. Description of Related Art

Conventionally, there are some kind of ophthalmic photographing apparatuses which photograph the anterior eye or fundus of the eye in order to submit its photographed images as data of diagnose.

When using the above apparatus, it is important that the photographing condition is kept stable so as to be able to find delicate changes of the affected part of the eye. Particularly, an apparatus for photographing an anterior eye is requested to find a minute successive change as opacity of the crystalline lens, so that the quality of the photographing apparatus depends on whether its photographing condition can be kept stable.

Because it is most important for the photographing apparatus to provide the photographing light at a constant amount, there are usually following methods to correct changes of the amount of the light emitted from the photographing light source during photograph. The first method is to adjust the amount of the light so as to be constant by monitoring the amount of the light emitted from the light source during photograph and feeding it back. The second method is to compensate the density and brightness of the image based on gray scale image projected over the image. Therefore, if using the above methods, it takes much time to photograph and diagnose the affected part of the eye.

SUMMARY OF THE INVENTION

The present invention has been made in view of the above circumstances and has an object to overcome the above problems and to provide an ophthalmic photographing apparatus which is able to photograph the eye to be examined precisely for a short time.

Additional objects and advantages of the invention will be set forth in part in the description which follows and in part will be obvious from the description, or may be learned by practice of the invention. The objects and advantages of the invention may be realized and attained by means of the instumentalities and combinations particularly pointed out in the appended claims.

To achieve the objects and in accordance with the purpose of the invention, as embodied and broadly described herein, ophthalmic photographing apparatus of this invention comprises memory means for memorizing the image data of the photographed eye, light detecting means for detecting an amount of the light emitted from a light source for photographing, and correcting means for correcting a density of the image data memorized in the memory means by comparing the amount of the light detected by the light detecting means with the amount of predetermined reference light, wherein a constant density of the image is obtained even though the amount of the light emitted from the light source for photographing changes.

According to the ophthalmic photographing apparatus of this invention, even though the amount of the light emitted from the photographing light source changes, the image having the constant density is able to be displayed by correcting the density of the photographed image. Further, the density of the photographed image is corrected after actual photographing process, it does not take much time to photograph, therefore the photographer can precisely photograph the eye to be examined by simple operation for a short time.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 1 is a schematic view of the ophthalmic photographing apparatus on the basis of Scheimpflug's principle.

FIG. 3 is a block diagram of the image signal level control system.

DETAILED DESCRIPTION OF THE PREFERRED EMBODIMENTS

Figure 2:
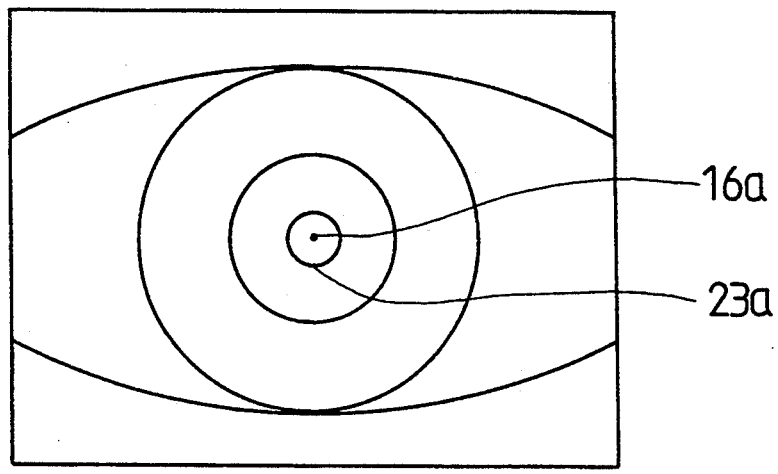
FIG. 2 is a front view of the alignment monitor.

A detailed description of one preferred embodiment of an ophthalmic photographing apparatus embodying the present invention will now be given referring to the accompanying drawings.

In FIG. 1, an optical system of a photographing apparatus for photographing sectionally the anterior eye on the basis of the Scheimpflug's principle is shown schematically.

The optical system comprises the slit projection optical system, the photographing optical system, the alignment fixation projection system, the alignment observing system, and the reticule projection system for alignment.

First, the slit projection optical system consists of a illumination light source 1 for projecting a slit image onto an anterior eye 12, an infrared irradiation transmitting filter 2, condenser lenses 3 and 4, a flash photographing light source 5, a slit 6 changeable its width as a conventional slit lamp, a polarizing filter 7 preventing the slit light from being incident into CCD camera for alignment 14 as mentioned later, a slit projection lens 8, a rectangular aperture diaphragm 9 by which the depth of focus of the slit projected image is made deeper, and a polarized beam splitter 10.

The light emitted from the flash light source 5 in the slit projection optical system is introduced into a (brightness level) detector 26 through a filter Z5 for reducing the amount of the light. On receiving the reduced light, the (brightness level) detector 26 monitors its amount.

In the photographing optical system, a focusing lens 13 and a CCD camera 14 are arranged so that an optical sectional plane of the projection image of the slit 6, an extended plane of a principal plane of the focusing lens 13 and that of a plane of CCD camera 14 intersect each other by one intersectionline. The photographing optical axis is arranged so as to be inclined to the slit projection optical axis with 45 degrees.

The alignment fixation projection optical system includes a light source for alignment 15 consisted of visible ray as LED, a index for fixation and for alignment 16 taking the form of a pin hole, a index projection lens 17, and a half mirror 18.

The alignment observing optical system is provided with a focusing lens 19, a half mirror 20 and a CCD camera for alignment 21.

The reticule projection optical system for alignment consists of a light source for reticule projection 22 using an infrared light, a reticule for alignment 23 having a ring form, and a reticule projection lens 24.

Further, in the above mentioned apparatus, the slit projection optical system of numerals 1~10, the photographing optical system of 13, 14 and the alignment fixation projection system of 15~18 are able to revolve around a visual axis of the eye to be examined 11, therefore the anterior eye can be sectionally photographed at two or more positions.

In FIG. 2, a monitor image photographed by the CCD camera 21 is shown, wherein numeral 16a is a reflected image of the index for fixation and for alignment on the front surface of cornea, and numeral 23a is the reticule image for alignment.

A block diagram of an image signal level control system for correcting changes of the amount of the light emitted from the photographing light source is shown in FIG. 3.

The image signal detected by the CCD camera 14 is amplified by an amplifier 31, converted into a digital signal through an analog/digital converter 32, and stored in a frame memory 33 as a picture element data "c".

The monitor signal of the (brightness level) detector 26 which receives the amount of light emitted from the flash light source 5 is amplified by an amplifier 27, and converted into a digital signal data "a" through an analog/digital converter 28, after that transmitted into the microcomputer 29.

On the other hand, a reference data of the amount of the light "b" is memorized in a nonvolatile memory 30 in advance, which data "b" is an average calculated of several monitor data of the amount of the light emitted from the light source.

Further, microcomputer 29 reads out the picture element data "c" from frame memory 33, and converts it into the picture element data "d" by calculating as a following formula, after that rebacks it to frame memory 33.

$$d=(b/a)\times c$$

Next, the picture data "d" in the frame memory 33 is converted into a analog image signal through the digital/analog converter 34, and amplified by an amplifier 35, and then displayed on CRT display 36.

As mentioned above, in CRT display 36, the image corrected changes of the amount of light of the flash light source 5 is displayed, therefore photographer can diagnose the eye to be examined more precisely.

According to the above apparatus, the operation is explained as follows. First, since the image of the index for fixation and alignment 16 is projected onto the patient's eye to be examined 11, the patient should fixedly stare at the image.

On the other hand, the reflected image of the index 16 on the front surface of the cornea of the eye 11 is monitored in the CCD camera 21 for alignment through an focusing lens 19. To set the alignment, while watching the monitored image in the CCD camera 21, the apparatus is moved in the right or left direction, further up or down so as to put the point reflected image 16a of the index 16 into the small circle of the reticule image 23a for alignment. Further, to set the alignment in the optical axis direction, the apparatus is moved forward or backward so that the point image 16a comes into focus.

It is possible to bring the photographing system in focus by moving the focusing lens 13 in the extending direction of its principal plane or by moving CCD camera 14 in that of the focus point, while watching the monitor of photographing CCD camera 14 (not shown).

Usually, the depth of focus is deep because the F-number of the focusing lens 13 is large, so that it is almost unnecessary to focus if the alignment is finally fixed.

After confirming that arrangement for photographing is complete, the photographer depresses a button for photographing (not shown) in order to emit the flash light source 5, so that the flash light emitted from the flash light source 5 illuminates the anterior eye through the same optical path as the slit illumination light.

Synchronous to the emitting light from the flash light source 5, the image signal detected by the CCD camera 14 is given to the frame memory 33, and the light monitor signal of the (brightness level) detector 26 is fetched.

The image signal detected and the light monitor signal are calculated in the image signal level control system (microcomputer 29) mentioned above in order to display the image corrected a change of the amount of the light emitted from the flash light source 5 on the CRT display 36.

Furthermore, because the corrected image signal can be kept by applying conventional methods, for example to store it in a disc, it is possible to find correctly the successive change of the image by previously comparing with the image stored.

The present invention may be embodied in other specific forms without departing from the spirit or essential characteristics thereof. For instance, in the above embodiment, although the image correcting operation in the photographing apparatus for photographing sectionally the anterior eye is explained, the same operation can be put in the other ophthalmic photographing apparatus.

Further, the (brightness level) detector for monitoring the amount of the light can be arranged in any position where is able to receive the light emitted from the photographing light source.

In the above embodiment, although the image signal and the light monitor signal are calculated in microcomputer by being converted into digital signals, it is possible to process the obtained analog signal or the analog signal and digital signal in hardware.

Furthermore, although in the correcting calculation mentioned above, the ratio of the reference light monitor value and light monitor value obtained by photographing is applied to, the same result can be obtained by calculating with another coefficient obtained under considering the character of the (brightness level) detector or with another functional equation.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for photographing an image of an eye to be examined, comprising:
   memory means for storing image data of the photographed eye;
   light detecting means for detecting an amount of light emitted from a light source for photographing; and
   correcting means for correcting a density of the image data stored in the memory means by comparing the amount of light detected by the light detecting means with a constant amount of light used as a reference,
   wherein a constant density of the image is obtained even though the amount of light, emitted from said light source for photographing, changes.

2. An opthalmic apparatus according to claim 1, wherein said light source for photographing is a flash light source, said light detecting means is a light detecting device, and said correcting means corrects the density of the image data by comparing a detected light data based on a light monitor signal from said light detecting device with a light data of the amount of reference light.

3. An opthalmic apparatus according to claim 1, wherein the image data of the eye to be examined which is stored in said memory means is obtained from the anterior of the eye.

4. An ophthalmic apparatus according to claim 1, wherein the image data of the eye to be examined which is stored in said memory means is obtained from the fundus of the eye.

5. An ophthalmic apparatus for photographing an image of an eye to be examined, comprising:
   a slit image projection system for projecting a slit image onto the eye to be examined;
   a photographing system for photographing the slit image projected on the eye to be examined by means of an image photographing means;
   memory means for storing as picture element data an image signal of the image on the eye photographed by said photographing means;
   a flash light source arranged in the slit image projection system for photographing the eye to be examined;
   light detecting means for detecting an amount of the light of said flash light source; and
   correcting means for correcting a density of the picture element data of the image of the eye stored in the memory means by comparing the detected amount of light data based on a light monitor signal inputted from the light detecting means with a determined amount of reference light data.

6. An opthalmic apparatus according to claim 5, wherein said image photographing means comprises a CCD camera.

7. An ophthalmic apparatus according to claim 5, wherein said light detecting means comprises a light detecting device.

8. An ophthalmic apparatus according to claim 5, further comprising:
   second memory means for storing said amount of reference light data in advance.

9. An ophthalmic apparatus according to claim 5, further comprising:
   an output display means for indicating the image on the eye to be examined based on the picture element data of the density corrected by said correcting means.

10. An ophthalmic apparatus for photographing an image of an eye to be examined, comprising:
    a slit image projection system for projecting a slit image onto the eye to be examined;
    a photographing system for photographing the slit image projected on the eye to be examined by means of an image photographing means;
    memory means for storing as picture element data an image signal of the image on the eye photographed by said photographing means;
    a flash light source arranged in said slit image projection system for photographing an eye to be examined;
    light detecting means for detecting an amount of the light of said flash light source; and
    correcting means for correcting a density of the picture element data of the image of the eye stored in the memory means by comparing the detected amount of light data based on a light monitor signal inputted from the light detecting means with a determined amount of reference light data,
    wherein the corrected density of the picture element data from said correcting means is calculated according to the following equation:

$$d = (b/a) \times c$$

where "a" is the detected light data, "b" is the reference light data, "c" is the picture element data of the image on the eye stored in the memory means in advance, and "d" is the corrected density of the picture element data.

11. An ophthalmic apparatus for photographing an image on an eye to be examined, comprising:
    a slit projection system for projecting a slit image onto the eye to be examined;
    a photographing system for photographing the slit image projected onto the eye to be examined by means of a first CCD camera;
    an alignment fixation projection system for projecting an alignment fixation image onto the eye to be examined;
    an alignment observing system for photographing the alignment fixation image projected onto the eye to be examined by means of a second CCD camera;
    a reticule projection system for photographing an alignment reticule image by means of said second CCD camera;
    memory means for storing as picture element data an image signal of the eye image photographed by means of said first CCD camera;
    a flash light source arranged in said slit image projection system for photographing the eye image;
    light detecting means for detecting an amount of light emitted from said flash light source; and
    correcting means for correcting a density of the picture element data of the image on the eye stored in the memory means by comparing detected light data based on a light monitor signal inputted from the light detecting means with a determined reference light data.

12. An ophthalmic apparatus according to claim 11, further comprising:
    second memory means for memorizing the reference light data in advance.

13. An ophthalmic apparatus according to claim 11, further comprising:

output display means for indicating the image of the eye to be examined based on the picture element data in the density corrected by said correcting means.

14. An ophthalmic apparatus for photographing an image on an eye to be examined, comprising:

a slit projection system for projecting a slit image onto the eye to be examined;

a photographing system for photographing the slit image projected onto the eye to be examined by means of a first CCD camera;

an alignment fixation projection system for projecting an alignment fixation image onto the eye to be examined;

an alignment observing system for photographing the alignment fixation image projected on tot he eye to be examined by means of a second CCD camera;

a reticule projection system for photographing an alignment reticule image by means of said second CCD camera;

memory means for storing as picture element data an image signal of the eye image photographed by means of said first CCD camera;

a flash light source arranged in said slit image projection system for photographing the eye image;

light detecting means for detecting an amount of light emitted from said flash light source; and correcting means for correcting a density of the picture element data of the image on the eye memorized in the memory means by comparing detected light data based on a light monitor signal inputted from the light detecting means with a determined reference light data, wherein the corrected density of the picture element data from the correcting means is calculated according to the following equation:

$$d = (b/a) \times c$$

where "a" is the detected light data, "b" is the basic light data, "c" is the picture element data of the image on the eye memorized in the memory means in advance, and "d" is the corrected density of the picture element data.

* * * * *